United States Patent
Hawman et al.

Patent Number: 5,462,056
Date of Patent: Oct. 31, 1995

[54] HIGH-SENSITIVITY SPECT IMAGING OF SMALL BODY ORGANS USING A MULTI-HEADSCINTILLATION CAMERA WITH NON-UNIFORM COLLIMATION

[75] Inventors: Peggy C. Hawman, Schaumburg; Jianzhong Qian, Hoffman Estates; Jon D. Treffert, Bartlett, all of Ill.

[73] Assignee: Siemens Medical Systems, Inc., Iselin, N.J.

[21] Appl. No.: 382,944

[22] Filed: Jan. 31, 1995

Related U.S. Application Data

[63] Continuation of Ser. No. 54,804, Apr. 27, 1993, abandoned, which is a continuation-in-part of Ser. No. 765,654, Sep. 25, 1991, and Ser. No. 848,769, Mar. 10, 1992, Pat. No. 5,381,791.

[51] Int. Cl.$^6$ .............................. G01T 1/161; G21K 1/02
[52] U.S. Cl. .............. 128/659; 250/363.02; 250/363.04; 250/363.1
[58] Field of Search ................................. 128/653.1, 654, 128/659; 250/363.02, 363.04, 363.05, 363.1; 378/19

[56] References Cited

U.S. PATENT DOCUMENTS

| | | | |
|---|---|---|---|
| 4,659,935 | 4/1987 | Hawman | 250/363.04 |
| 4,670,657 | 6/1987 | Hawman et al. | 250/363.04 |
| 4,752,691 | 6/1988 | Hawman | 250/363.1 |
| 4,849,638 | 7/1989 | Hawman | 250/363.1 |
| 4,859,852 | 8/1989 | Genna et al. | 250/363.1 |
| 5,001,347 | 3/1991 | Hsieh | 250/363.1 |
| 5,055,687 | 10/1991 | Ichihara | 250/363.02 |
| 5,059,799 | 10/1991 | Kurakake | 250/363.02 |
| 5,075,554 | 12/1991 | Yunker et al. | 250/363.04 |
| 5,206,512 | 4/1993 | Iwao | 250/363.05 |

FOREIGN PATENT DOCUMENTS

| | | |
|---|---|---|
| 0250249 | 12/1987 | European Pat. Off. |
| 0289737 | 11/1988 | European Pat. Off. |
| 0465952 | 1/1992 | European Pat. Off. |

OTHER PUBLICATIONS

Ronald J. Jaszczak et al., Three–Dimensional Spect Reconstruction of Combined Cone Beam and Parallel Beam Data, Phys. Med. Biol., 1992, vol. 37, No. 3, pp. 535–548.

*Primary Examiner*—Krista M. Zele
*Attorney, Agent, or Firm*—Mark H. Jay

[57] ABSTRACT

A multi-head SPECT-capable scintillation camera has one head collimated by a parallel hole collimator and one or more focussing collimators. The focussing collimators are advantageously cone beam collimators or (for scintillation cameras which have rectangular detectors) astigmatic collimators. The scintillation camera is used to acquire information about a relatively small body organ of interest, such as the heart or the brain. From this information, the spatial location of the organ is determined. Then, during rotation of the camera heads about the patient during a SPECT study, the positions of the focussing collimators are controlled so as to maintain the organ of interest in a predetermined position with respect to their field(s) of view. Thereafter, the data acquired during the SPECT study is used to form a SPECT image of the organ of interest. The SPECT image may then be displayed or outputted.

17 Claims, 7 Drawing Sheets

HIGH-SENSITIVITY SPECT IMAGING OF SMALL BODY ORGANS USING A MULTI-HEAD SCINTILLATION CAMERA WITH NON-UNIFORM COLLIMATION

CROSS-REFERENCE TO RELATED APPLICATIONS

This application is a continuation of application Ser. No. 08/054,804 filed Apr. 27, 1993, now abandoned which is a continuation-in-part of commonly-owned patent applications application Ser. Nos. 07/765,654 filed Sep. 25, 1991 (hereinafter "Treffert") and 07/848,769 filed Mar. 10, 1992 (hereinafter "Qian") now U.S. Pat. No. 5,381,791. The entire disclosures of these applications, including the drawings, are hereby incorporated into this application as if fully set forth herein.

BACKGROUND OF THE INVENTION

The invention relates to nuclear medicine, and more particularly relates to nuclear medicine SPECT studies. In its most immediate sense, the invention relates to SPECT studies of relatively small body organs, such as the heart and the brain, carried out using a SPECT-capable scintillation camera having more than one detector (a "multihead" scintillation camera).

In a nuclear medicine study of a body organ of interest, a radioisotope is administered to a patient and taken up in the body Organ. The patient is then placed in a scintillation camera, which has one or more detectors ("heads"). Each head contains a scintillator (usually a NaI(Tl) crystal). As the radioisotope undergoes radioactive decay, it gives off gamma radiation. This gamma radiation is collimated and directed in its collimated state to the scintillators. As the gamma radiation interacts with the scintillators, flashes of scintillation light ("scintillation events") occur in the scintillators. Photodetectors (conventionally, photomultiplier tubes or "PMTs") are optically coupled to the scintillators and respond to the scintillation events by producing electrical signals. Such signals, after appropriate signal processing, contain information which is used to form images that show where the radioisotope has been taken up. Such images are used by radiologists to identify pathology of the body organ which is the subject of the study.

For some diagnostic applications, the images are two-dimensional ones. Studies which produce such images are called planar imaging studies. In planar imaging studies, data is collected while the camera heads are fixed in position. However, most modern diagnostic applications require tomographic (three-dimensional) images of the distribution of the radioisotope (the "activity") within the organ of interest. Studies which produce such three-dimensional images are known as SPECT (Single Photon Emission Computed Tomography) studies. In conventional SPECT studies the camera heads are rotated around the patient by a gantry so as to sample the entire activity within and surrounding the organ of interest. With the information thus obtained, it is possible to use mathematical techniques (so-called "backprojection" techniques) to computer-reconstruct a three-dimensional SPECT image of the activity within the organ of interest.

The heart and the brain are relatively small as compared with the sensitive crystal surface in conventional scintillation camera detectors. It is therefore conventional practice to use focussing collimators (e.g. cone beam collimators, astigmatic collimators) when imaging such organs. This magnifies the image of the organ as "seen" by the detector and therefore increases sensitivity.

Where a SPECT study of a small body organ is carried out using only a focussing collimator (e.g. a cone beam collimator), image distortions ("reconstruction artifacts") appear in the reconstructed SPECT image. This is because a focussing collimator does not adequately sample the entire activity distribution around the organ of interest (even though a focussing collimator may adequately sample the entire activity distribution within the organ of interest.) Dr. Jaszczak et al. of Duke University have therefore proposed (see *Three-Dimensional SPECT Reconstruction of Combined Cone-Beam and Parallel-Beam Data*, Phys. Med. Biol. 37:535–548, 1992) that such studies be carried out using a cone beam collimator and a parallel hole collimator at the same time. Because the parallel hole collimator samples the entire activity distribution, the focussed and nonfocussed data can be combined to produce a SPECT image which not only benefits from the magnification afforded by the focussing collimator, but which nonetheless lacks the reconstruction artifacts which are caused by inadequate sampling.

Although this technique holds out the prospect of improving SPECT images produced by multi-head SPECT-capable scintillation cameras, SPECT studies are still lengthy. This is because constraints imposed by use of conventional cone beam collimation in SPECT studies limit sensitivity of the system. Substantial time is needed to acquire the necessary SPECT data.

It would therefore be advantageous to provide method and apparatus for increasing the sensitivity of SPECT studies carried out on multi-head scintillation cameras using both focussing and parallel hole collimators.

The invention proceeds from the realizations that a) a focussing collimator produces maximum sensitivity improvements when the organ of interest is as far away from the collimator as possible and b) a focussing collimator will adequately sample the activity within the organ of interest if the organ is always completely encompassed within the field of view of the collimator. It follows from these known facts that if this relationship could be maintained throughout the entire SPECT study, maximum use would be made of the sensitive crystal surface but truncation artifacts would not come about.

In accordance with the invention, a multi-head SPECT-capable scintillation camera has one detector which is collimated using a parallel hole collimator. Another detector, or more than one other detectors, are collimated using focussing collimators.

When a SPECT study of a small body organ such as the heart or the brain is to be conducted, the scintillation camera is used to acquire information about the organ. Based on this information, the organ of interest is located in space (with respect to the scintillation camera). Once the organ of interest has been located in space, the camera is operated in such a manner as to maintain the organ of interest in a predetermined optimum position with respect to the field(s) of view of the focussing collimator(s), throughout the entire rotation of the camera heads around the patient. In the normal case, this optimum position is the furthest possible distance from the camera head without causing the organ to project beyond the field(s) of view of the focussing collimator(s) and to thereby cause truncation artifacts.

Advantageously, and in accordance with a presently preferred embodiment of the invention, the location of the organ of interest is initially determined and the patient bed is subsequently moved so as to situate the organ of interest at a predetermined location within the scintillation camera.

Once this has been done, a SPECT study is carried out in the normal manner, with appropriate radial movement of the camera heads to maintain the proper relative positioning of the organ with respect to the focussing collimators.

In the conventional case, the focussing collimator(s) are of the cone beam type because reconstruction algorithms have already been developed for this type of collimator when it is used together with a parallel hole collimator. However, where the detectors are rectangular, as in the MULTISPECT scintillation cameras manufactured by Siemens Gammasonics, Inc., owner of this and the above-stated two parent patent applications, it is especially advantageous if the focussing collimators are of the astigmatic type (see, e.g., commonly owned U.S. Pat. No. 4,670,657). This is because such collimators have two focal lines and these can be selected so as to optimally mate the characteristics of the collimator to the rectangular shape of the detectors.

To locate the organ of interest in space, the techniques disclosed in either or both of the above-referenced parent patent applications can be used.

BRIEF DESCRIPTION OF THE DRAWINGS

The invention will be better understood with reference to the following illustrative and non-limiting drawings, in which.

DETAILED DESCRIPTION OF THE PREFERRED EMBODIMENTS

For the sake of clarity, all the Figures are exaggerated and are not to scale. Additionally, the same element is always indicated by the same reference numeral.

Figure 1:
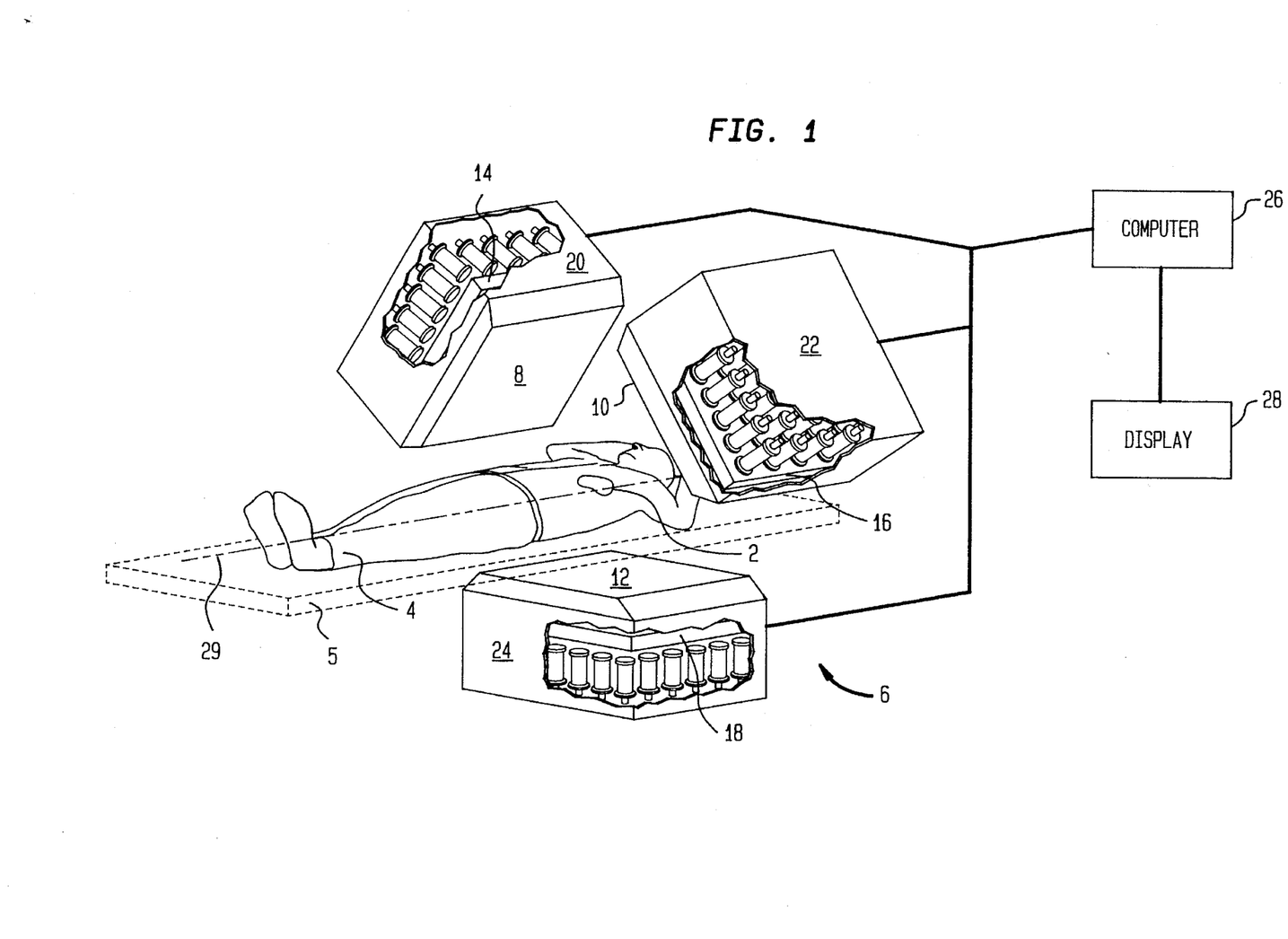
FIG. 1 schematically illustrates a SPECT study carried out using a conventional scintillation camera system.

FIG. 1 schematically illustrates a nuclear medicine study of the heart 2 of a patient 4 being carried out using a conventional SPECT-capable scintillation camera system now being manufactured by Siemens Gammasonics, Inc. under the MULTISPECT 3 trademark and generally indicated by reference numeral 6. The patient 4 is supported upon a patient bed 5.

A radioisotope (not shown) is administered to the patient 4 and collects in the heart 2. As the radioisotope decays, gamma radiation is released. This radiation is collimated by the three collimators 8, 10, 12 of the camera system 6, and the collimated radiation is directed to scintillators 14, 16, 18 in the three detectors 20, 22, 24 of the camera system 6. Electrical signals (not shown) produced by the detectors 20, 22, 24 are subjected to signal processing and a computer 26 is used to reconstruct images of the heart 2. Such images can be displayed on display 28. In a SPECT study of the heart 2, the detectors 20, 22, 24 are rotated around the patient by a gantry (not shown) to sample all of the activity in the heart 2. Reference numeral 29 indicates the central axis of the camera system 6.

Figure 2A:
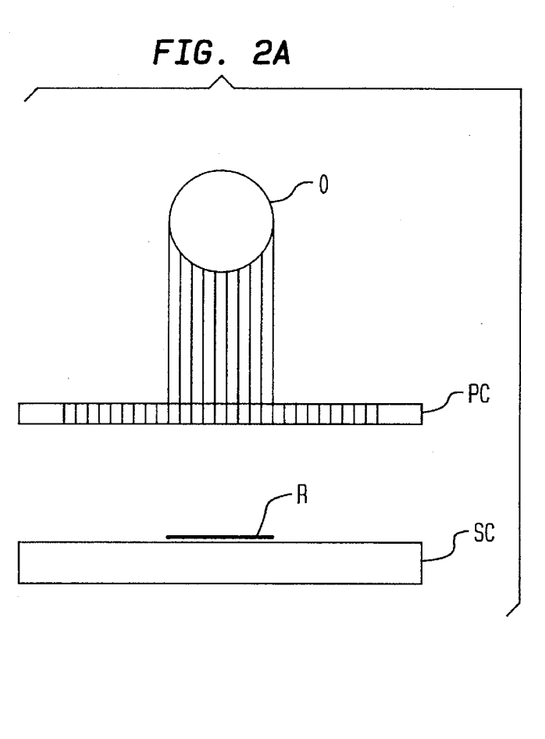
FIG. 2 and 2B schematically illustrates the sensitivity improvement which a focussing collimator brings about when imaging a small body organ.
Figure 2B:
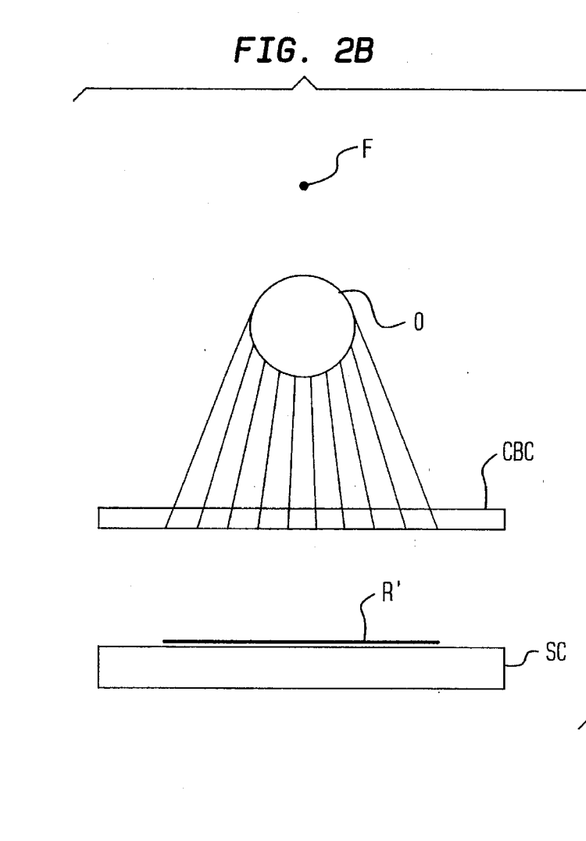

FIG. 2A and 2B schematically illustrates the sensitivity improvement which a focussing collimator brings about when a small body organ is the subject of a nuclear medicine study. As can be seen in FIG. 2A, where a parallel hole collimator PC is used to form an image of a small body organ O, a relatively small region R of the scintillation crystal SC receives information about the organ O. However, where (see FIG. 2B) a cone beam collimator CBC is used to form an image of the organ O, the corresponding region R' on the scintillation crystal SC is much larger. Therefore, since a much larger area on the scintillation crystal SC receives information about the organ O, the sensitivity of the study is improved.

Figure 3A:
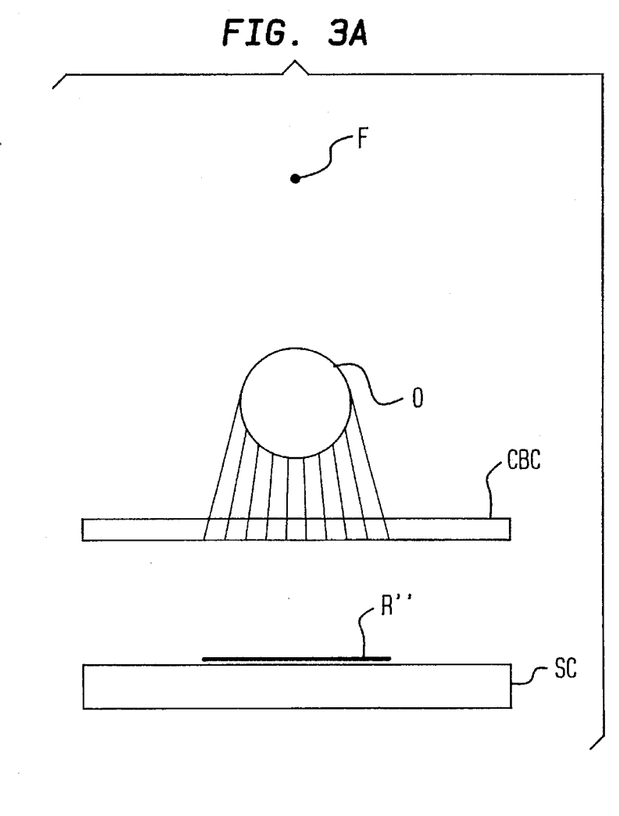
FIG. 3 and 3B schematically illustrates the effect of organ position on sensitivity when a focussing collimator is used.
Figure 3B:
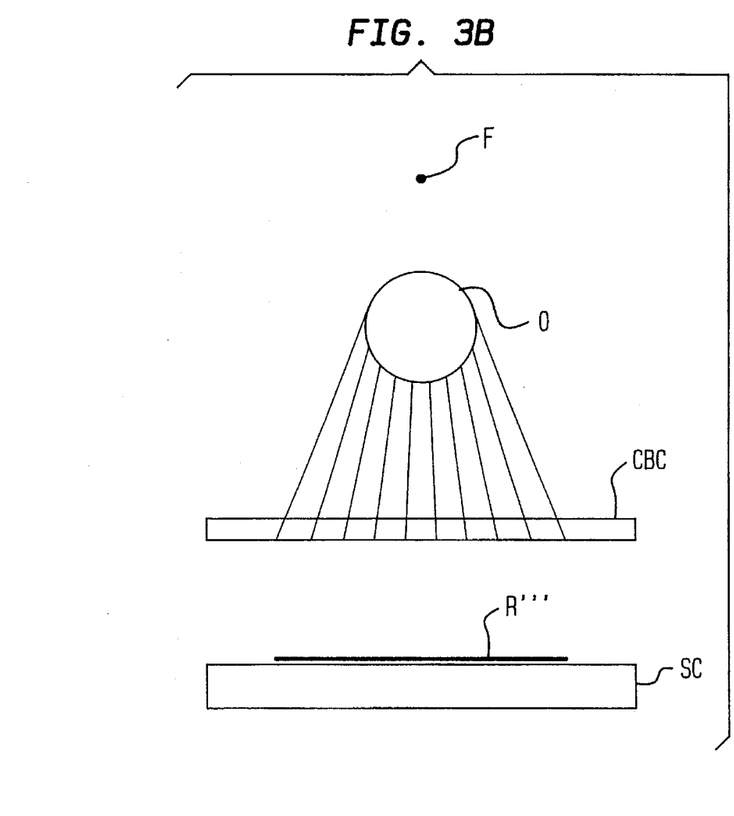

FIG. 3A and 3B schematically illustrates the effect of organ position on sensitivity when a focussing collimator is used. Where (see FIG. 3A) the organ O is comparatively close to the cone beam collimator CBC, the information-receiving region R" is relatively small. However, where (see FIG. 3B) the organ O is closely adjacent the focal point F of the cone beam collimator CBC, the information-receiving region R'" is much larger. Thus, sensitivity can be maximized by keeping the organ O centered within the field of view of the collimator and keeping the organ O as far away from the collimator as possible while making sure the organ O remains entirely within the field of view.

Figure 4:
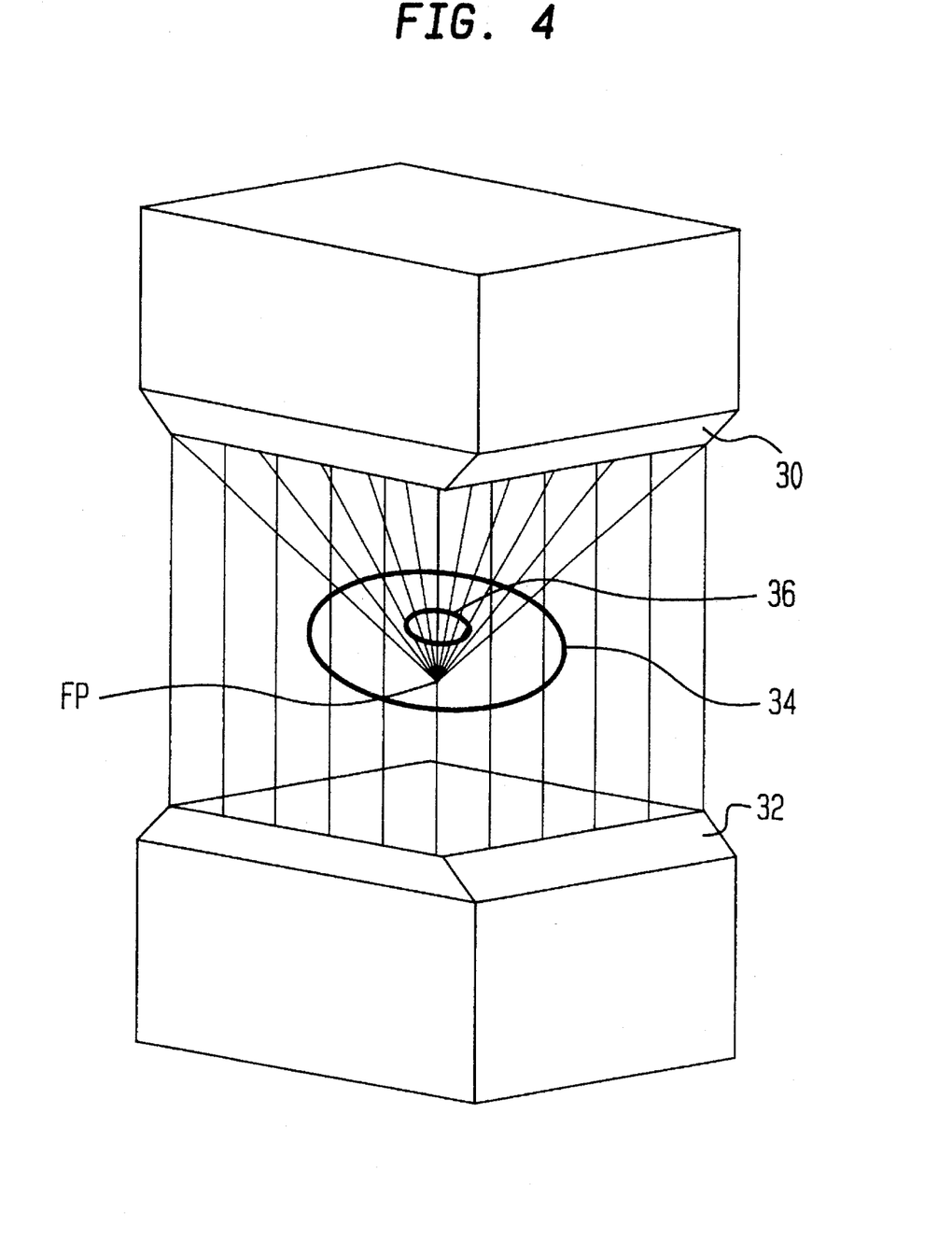
FIG. 4 schematically illustrates a first preferred embodiment of apparatus in accordance with the invention.

In accordance with a first embodiment according to the invention and schematically illustrated in FIG. 4, a two-head SPECT-capable scintillation camera (not shown) such as is manufactured by Siemens Gammasonics, Inc. under the MULTISPECT 2 trademark is collimated with a cone beam collimator 30 and a parallel hole collimator 32. Initially, a patient 34 is introduced into the camera on a patient bed which is shown schematically and indicated by reference numeral 5. Then, the camera is used to acquire information about the small body organ of interest (in this instance, the heart 36). With this information, the heart 36 can be located in space (i.e. with respect to the camera). This can be done using the methods and apparatus disclosed in the above-referenced Treffert and Qian applications.

Once this information is known, the camera is so operated during a SPECT study of the heart 36 as to cause the heart 36 to be maintained in a position which is centered within the field of view of the cone beam collimator 30, close to the focal point FP of the cone beam collimator 30. This is presently believed to be most advantageously done by moving the patient bed 5 (see FIG. 1) so as to place the heart 36 along the central axis 29 (see FIG. 1) of the scintillation camera system and then appropriately controlling the operation of the camera gantry (not shown) in accordance with the method and apparatus disclosed in the above-referenced parent patent applications to Treffert and Qian; as the collimators 30, 32 are rotated about the patient 34, the radial position of the cone beam collimator 30 is adjusted so that the heart 36 is maintained at this predetermined position. (It may not be possible to implement the present invention on a conventional MULTISPECT camera system; modification may be required and this is now under investigation.) After completion of the study, the acquired data is processed, a SPECT image is reconstructed and outputted for diagnostic use.

At present, it is believed that it is most advantageous to maintain the organ of interest (in this instance, the heart 36) entirely within the field of view of the cone beam collimator 30. However, it may be that truncation artifacts caused by minor or occasional excursions of the organ of interest outside the field of view may not unduly degrade the reconstructed SPECT image. Thus, while it is advantageous to prevent the organ of interest from leaving the field of view of the focussing collimator, this is not strictly necessary.

Figure 5:
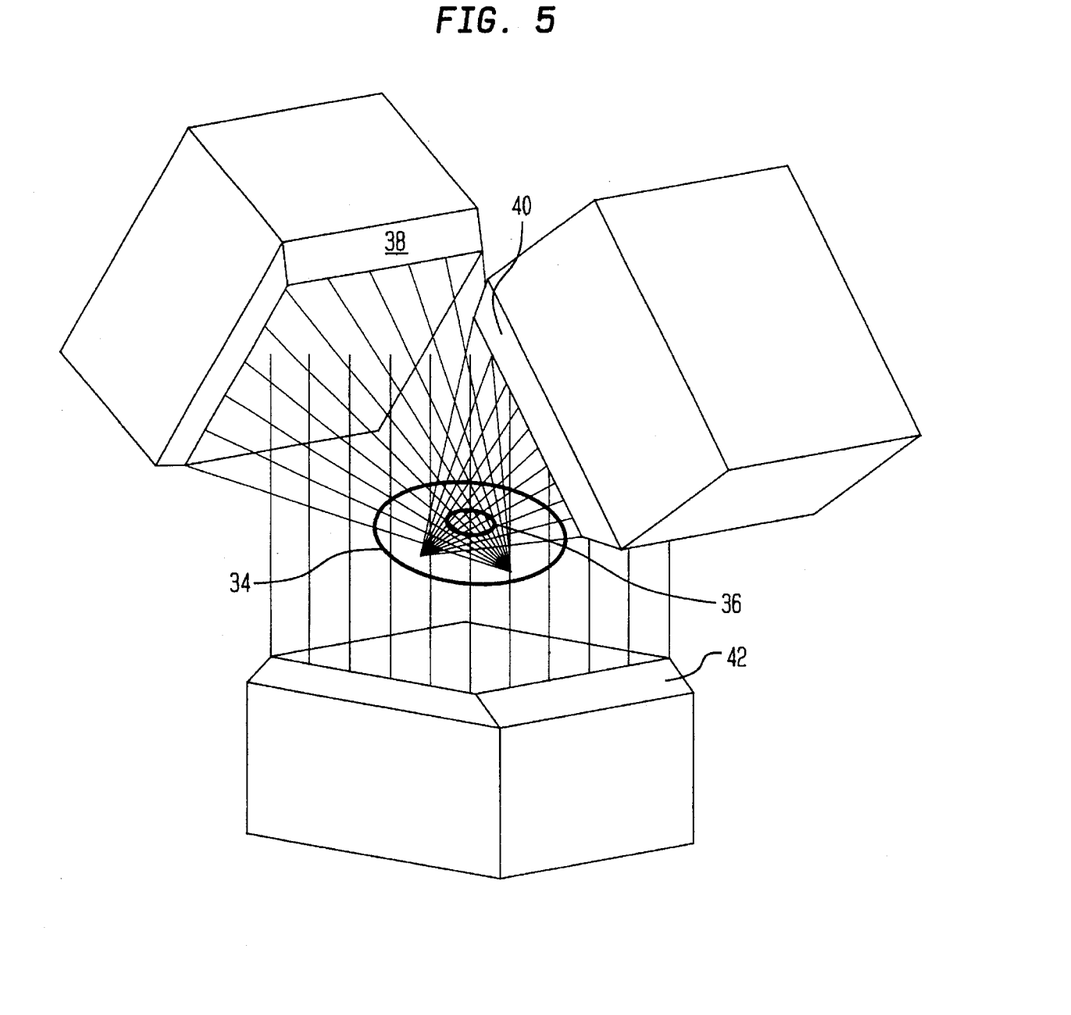
FIG. 5 schematically illustrates a second preferred embodiment of apparatus in accordance with the invention.
Figure 6:
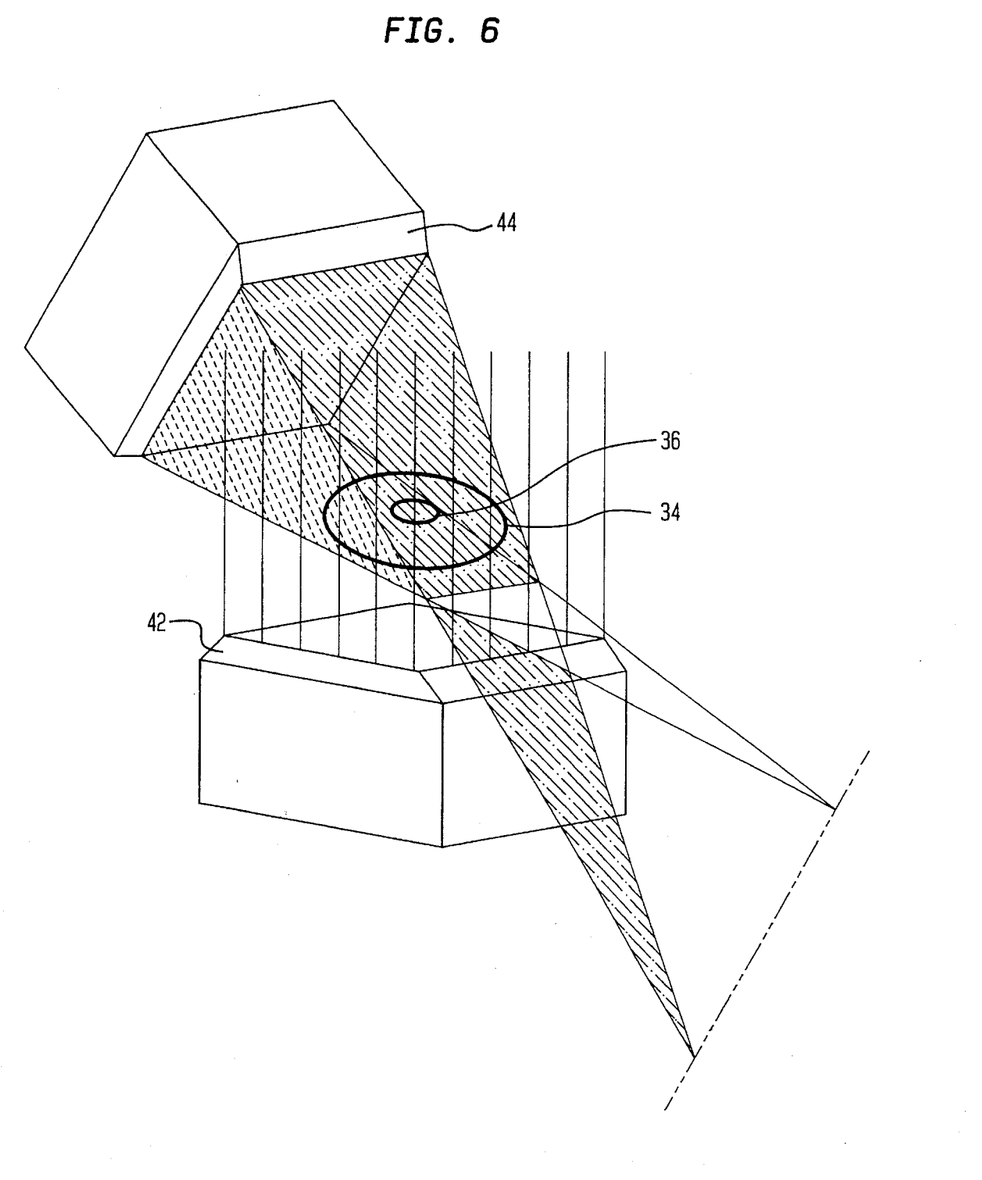
FIG. 6 schematically illustrates a third preferred embodiment of apparatus in accordance with the invention.

In a second preferred embodiment which is illustrated in FIG. 5 and which uses a three-head camera (not otherwise shown), the collimators 38 and 40 are cone beam collimators and the collimator 42 is a parallel hole collimator. As described above, the patient bed 5 is initially operated so as to place the heart 36 along the axis 29 of the scintillation camera system. Then, the radial positioning of the collimators 38 and 40 is adjusted as the heads rotate around the patient 34 so that the heart 36 is maintained at the same predetermined position in the fields of view of the collimators 38 and 40.

Where the detectors of the camera are rectangular, as in the case of the detectors used in the MULTISPECT 3 and MULTISPECT 2 cameras manufactured by Siemens Gammasonics, Inc., assignee of the present application, a third preferred embodiment illustrated in FIG. 6 is especially advantageous. In accordance with this third preferred embodiment, each focussing collimator 44 is an astigmatic collimator in accordance with U.S. Pat. No. 4,670,657. This is because such collimators have two focal lines (16 and 18, in the specification for U.S. Pat. No. 4,670,657) which advantageously may be perpendicular to each other and dimensioned to correspond to the proportions of the camera detectors. In FIG. 6, this embodiment is shown installed in a three-head camera and the third head is not shown for clarity, but this embodiment could equally well be installed in a two- or more-than-three-headed camera.

Figure 7:
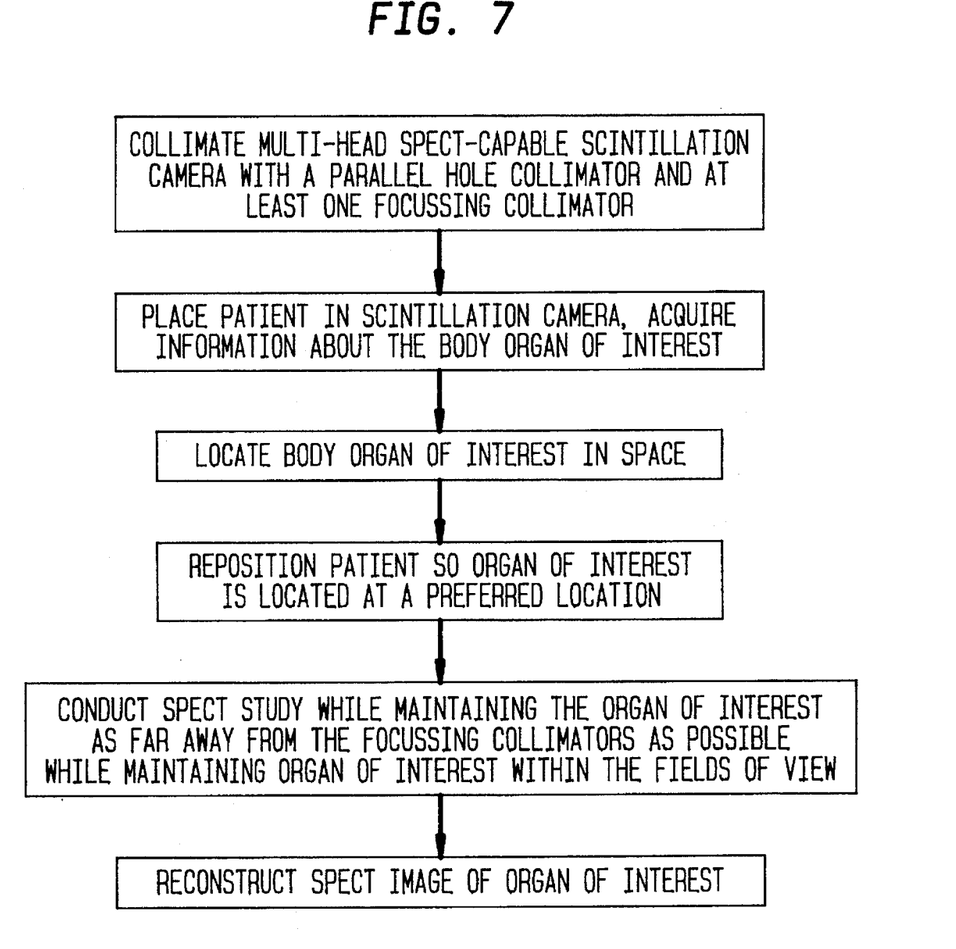
FIG. 7 is a flow chart of a preferred embodiment of a method in accordance with the invention.

FIG. 7 is a flow chart of a preferred embodiment of a method in accordance with the invention. As is shown there, a multi-head scintillation camera is collimated with a parallel hole collimator and at least one focussing collimator. Next, a patient is placed in the scintillation camera and the camera is used to acquire information about a relatively small organ of interest (e.g. the heart or brain). In accordance with the method and apparatus disclosed in the above-referenced parent patent applications to Treffert and Qian, this information is used to locate the organ in space.

Then, in accordance with the method and apparatus disclosed in the above-referenced parent patent applications to Treffert and Qian, the gantry and/or patient bed of the scintillation camera is/are controlled to maintain the organ of interest at a predetermined location with respect to the field(s) of view of the focussing collimator(s), throughout the rotation of the camera heads about the patient. Advantageously, this is done by initially repositioning the patient so as to locate the organ of interest at a preferred location, and thereafter adjusting the radial positioning of the camera heads as they rotate around the patient. Thereafter, the accumulated data is processed and used to produce a SPECT image of the organ of interest; this image may be displayed on a display or output on a printer.

Although a preferred embodiment has been described above, the scope of the invention is limited only by the following claims:

We claim:

1. A method of conducting a Single Photon Emission Computed Tomography SPECT study on a patient so as to produce a high-quality image of a relatively small organ of interest, comprising the following steps:

placing the patient in a SPECT-capable scintillation camera which has one detector collimated with a parallel hole collimator and at least one detector collimated with a focussing collimator;

acquiring information using the scintillation camera;

locating the organ of interest in space on the basis of said information; and conducting a SPECT study of the patient in such a manner that each of said at least one detectors is maintained in a predetermined geometrical relationship with the organ of interest.

2. The method of claim 1, wherein there is a focussing collimator for each of said at least one detectors and there is a one-to-one correspondence between all of said at least one detectors and all of the focussing collimators, and wherein all of the focussing collimators are of the same type.

3. The method of claim 2, wherein all of the focussing collimators are of the type which focus in two directions.

4. The method of claim 3, wherein all of the focussing collimators are of the cone beam type.

5. The method of claim 3, wherein all of the focussing collimators are of the astigmatic type and all the detectors are rectangular.

6. The method of claim 3, wherein the SPECT-capable scintillation camera has three detectors, one of said detectors being collimated with a parallel hole collimator and two of said detectors being collimated with cone beam collimators.

7. The method of claim 1, wherein the conducting step is carried out in such a manner that the organ of interest is maximally distant from the focusing collimator while still being entirely encompassed within all fields of view of the focussing collimators.

8. The method of claim 1, wherein said conducting step comprises the steps of initially repositioning the patient and subsequently adjusting radial positioning of the detectors as they rotate around the patient while keeping the position of the patient fixed.

9. A method of conducting a Single Photon Emission Computed Tomography SPECT study on a patient so as to produce a high-quality image of the heart, comprising the following steps:

placing the patient in a SPECT-capable scintillation camera which has one detector collimated with a parallel hole collimator and at least one detector collimated with a focussing collimator;

acquiring information using the scintillation camera;

locating the heart in space on the basis of said information;

repositioning the patient to relocate the heart to a predetermined advantageous location within the scintillation camera; and conducting a SPECT study of the patient in such a manner that the heart is maintained as far away as possible from said at least one focussing collimator while being entirely contained within the field of view of said at least one focussing collimator.

10. The method of claim 9, wherein all focussing collimators are selected from a class consisting of cone beam collimators and astigmatic collimators.

11. The method of claim 9, wherein the SPECT-capable scintillation camera is selected from a class consisting of two-head cameras and three-head cameras.

12. Apparatus for conducting a Single Photon Emission Computed Tomography SPECT study of a relatively small organ of interest within a patient, comprising:

a SPECT-capable scintillation camera into which the patient may be introduced, said camera having one detector collimated with a parallel hole collimator and at least one detector collimated with a focussing collimator;

computer means for locating the organ of interest in space based upon information accumulated by the scintillation camera;

means for rotating the detectors around the patient in such a manner that each of said at least one detectors is maintained in a predetermined geometrical relationship with the organ of interest; and means for creating and displaying a SPECT image of the organ of interest.

13. The apparatus of claim 12, wherein the detectors are rectangular.

14. The apparatus of claim 13, wherein said at least one focussing collimators is an astigmatic collimator.

15. The apparatus of claim 12, wherein said at least one focussing collimator is a cone beam collimator.

16. The apparatus of claim 12, wherein the SPECT-capable scintillation camera has two heads.

17. The apparatus of claim 12, wherein the SPECT-capable scintillation camera has three heads.

* * * * *